(12) United States Patent
Yoshpe et al.

(10) Patent No.: US 8,758,836 B2
(45) Date of Patent: Jun. 24, 2014

(54) METHOD AND FORMULATION FOR TREATING DRY EAR INFLAMMATION WITH CORTISONE

(76) Inventors: Nina S. Yoshpe, Huntington Beach, CA (US); Ayal Willner, Newport Beach, CA (US)

( * ) Notice: Subject to any disclaimer, the term of this patent is extended or adjusted under 35 U.S.C. 154(b) by 87 days.

(21) Appl. No.: 13/229,160

(22) Filed: Sep. 9, 2011

(65) Prior Publication Data
US 2013/0064911 A1 Mar. 14, 2013

(51) Int. Cl.
*A61K 36/886* (2006.01)
*A61K 36/48* (2006.01)
*A61K 36/00* (2006.01)

(52) U.S. Cl.
USPC ........... 424/744; 424/757; 424/769; 424/775; 424/725

(58) Field of Classification Search
None
See application file for complete search history.

(56) References Cited

U.S. PATENT DOCUMENTS

| | | | |
|---|---|---|---|
| 4,961,927 A | 10/1990 | Kogure | |
| 6,093,417 A * | 7/2000 | Petrus | 424/437 |
| 6,521,213 B1 * | 2/2003 | Mautone | 424/45 |
| 6,818,232 B1 | 11/2004 | Redmond et al. | |
| 7,879,372 B2 | 2/2011 | Yoshpe et al. | |
| 8,030,362 B2 * | 10/2011 | Eilat | 514/2.4 |
| 2002/0013305 A1 * | 1/2002 | Hanna | 514/178 |
| 2002/0076383 A1 * | 6/2002 | Mautone | 424/45 |
| 2004/0101506 A1 | 5/2004 | Fust | |
| 2004/0126414 A1 * | 7/2004 | Michaelis | 424/446 |
| 2005/0043251 A1 * | 2/2005 | Lane | 514/28 |
| 2007/0264362 A1 * | 11/2007 | Yoshpe et al. | 424/744 |
| 2008/0075670 A1 * | 3/2008 | Eilat | 424/43 |
| 2008/0167281 A1 * | 7/2008 | Preston | 514/171 |
| 2008/0299233 A1 * | 12/2008 | Yoshpe et al. | 424/744 |
| 2009/0111780 A1 * | 4/2009 | Giordano | 514/171 |

OTHER PUBLICATIONS

Underbrink, M. Grand Round Presentation, UTMB, Dept. of Otolaryngology. Mar. 2001. 6 pages. Obtained from website www.utmb.edu/otoref/grnds/Ear-Ext-Infect-2001-03.pdf.*
"Cortisporin Solution Facts and Comparisons", at http://www.drugs.com/cdi/cortisporin-solution.html, Jun. 3, 2011.
"Cortisporin Ophthalmic Suspension Side Effects", at http://www.drugs.com/sfx/cortisporin-ophthalmic-suspension-side-effects.html, Jun. 3, 2011.

* cited by examiner

*Primary Examiner* — Chris R Tate
(74) *Attorney, Agent, or Firm* — Hackler Daghighian & Martino

(57) ABSTRACT

The present invention provides a method and formulation for treating and preventing asteatosis or "dry ear" symptoms and inflammation. The method of the present invention comprises topically applying to the ear canal a semi-viscous diglycerin and butylene glycol polyhydroxy liquid formulation including hydrocortisone, a natural product anti-irritant, a wound healing agent, and an anti-inflammatory agent, stabilized with a cationic surfactant and a nonionic surfactant.

14 Claims, No Drawings

METHOD AND FORMULATION FOR TREATING DRY EAR INFLAMMATION WITH CORTISONE

BACKGROUND OF THE INVENTION

The present application incorporates U.S. Pat. No. 7,879,372 issued Feb. 1, 2011 herewith in its entirety.

1. Field of the Invention

This invention relates to the treatment of diseases and conditions associated with inflammation of the inner ear of a mammal, e.g. humans or pets, caused by asteatosis or "dry ear" comprising applying a semi-viscous, lipid base formulation with hydrocortisone to the affected tissue.

2. Related Art

Asteatosis, known as "dry ear", is a common condition of the external auditory canal where the skin, tissue, and fibrocartilaginous surfaces of the ear canal are dry and lack cerumen production and protection. This condition is sometimes associated with aging, over-cleaning, or chronic conditions such as diabetes or other serious diseases or conditions.

The cerumen earwax lubricates and prevents desiccation and burning of the skin within the ear canal, or external ear and middle ear (known as asteatosis). Because of the lack of cerumen which is protective of the ear canal, there is a change in the moisture balance and pH of the canal which may make it more prone to external ear infection causing dryness or desiccation of the canal skin leading to itching, scratching, and irritated ear canal surfaces. Antimicrobial protective properties of cerumen are due principally to the presence of fatty acids and a slightly acidic pH ~6. The lubricative properties of cerumen arise from the high content of the sebum produced by the sebaceous glands. Wet earwax, or cerumen, may contain lipids including, squalene, long-chain fatty acids, and alcohols. Pathogenic and nonpathogenic bacteria and fungi may dominate the flora of the canal causing overgrowth and actual infection. These infections can often time be very difficult to clear up requiring multiple office visits, particularly if there is fungal overgrowth. It is at this point that many patients will insert cotton tip applicators and other foreign bodies in the canal to alleviate the discomfort thereby stripping the protective coating of earwax that protects the skin lining of the ear canal. As a result, the ear canal may suffer from atopic dermatitis, desiccation, or more serious skin infection such as otitis external. Traditionally, patients seek medical assistance after the infection has occurred.

Another type of otitis externa that occurs mainly in elderly diabetics can develop due to a severely compromised immune system. Malignant otitis externa infects the bony ear canal and the soft tissues deep to the bony canal creating an unrelenting and inoperable pain. It must be treated with antibotics or it can spread deeper into the head and involve the bones of the skull base, constituting skull base osteomyelitis.

Conductive hearing loss happens when there is a problem conducting sound waves anywhere along the route through the outer ear, eardrum, or middle ear. It is presumed high frequencies produce a large vibration at the end near the middle ear, the eardrum detects and simplifies incoming air pressure waves for loudness, and the basilar membrane of the inner ear separates out different frequencies in a human. The physical condition of the ear, including the ear canal skin, tissue, and fibrocartilaginous surfaces should be maintained for overall healthy ear and sound recognition and preventing infection or ear disorders.

"Swimmer's ear", or ear ache, symptoms include swelling of the ear canal which may not be present in "dry ear" symptoms and ear canal tissue conditions. Ear inflammation is typically reported with "swimmer's ear" whereby a swimmer receives contaminated water or retains moisture in the ear causing it to succumb to microbial growth (most often pseudomonas) and the use of alcohols and drying solvents to treat this condition are described in the prior art (see Fust US 2004/0101506, Kogure U.S. Pat. No. 4,961,927, and Redmond U.S. Pat. No. 6,818,232). Fust teaches a method and composition for treating otitis externa, swimmer's ear, which soothes irritated ear canals and reduces inflammation. Fust (US 2004/0101506) focuses on the treatment of swimmer's ear, infection and some of its many bacteria or fungi forms, earwax, ear pressure and hearing loss, adverse reactions to antibiotics, all which result in symptoms similar to swimmer's ear (paragraphs [0001-0006]). There is a lack of predictability or exactness in prior art and correlation between the symptoms, diseases, and cures for ear treatment. "A wide variety of protocols for treating otitis externa may be complicated with immune system response and complications in treating "swimmer's ear" and cannot be routinely optimized" (FUST paragraphs [0007 through 0009]). "While the medical community has a wide variety of protocols available for the symptomatic treatment of otitis externa and other bacterial and/or fungi related diseases, it appears that little or no attention has been given to prevention of the disease. Fust teaches a wide variety of organisms and/or complicated conditions are commonly labeled "swimmer's ear" including a list of over 43 known organisms that cause otitis externa (paragraph [0002]). There is speculation in equating "swimmer's ear", or ear ache, with "dry ear" symptoms.

In treating the desiccation of skin surfaces and the absorption or adsorption of the medication, the base of a topical medication is often as important as the medication itself. A medication's potency often is changed with its base. It is important to receive a medication applied to the skin, in the correct base, for example as a liquid topical solution, lotion, cream, or ointment. Manufacturers of each topical product have control over the content of the base of a medication.

Many base topical solutions and mixtures for removing water from and drying the ear canal include drying alcohols such as isopropanol. Alcohol is a common liquid base used to clean out the ear, especially of pets, because it dissolves the natural oils and fats present in the ear, but alcohol is also drying, leaving the ear and skin red and irritated. Alcohol evaporates quickly removes water and thereby often over-dries the ear tissue and leaves it red and irritated.

Additionally, a mixture of acetic acid and water or acetic acid and alcohol are also common liquid bases used to clean ears, for example drops containing dilute acetic acid (vinegar diluted 3:1). While such mixtures are effective in killing bacteria and in eliminating yeast infections, they are not pH balanced, may over-dry, and may irritate or actually burn ear tissues.

Another topical solution liquid base, hydrogen peroxide, is also often used as an oxidizer or drying agent, and is an anti-microbial disinfectant used as a medical and oral debriding agent and for cleaning wounds and removing dead tissue. Hydrogen peroxide is absorbed by skin upon contact and creates a local skin capillary embolism that stops wound bleeding which appears as a whitening of the skin. Hydrogen peroxide, however, is not an effective solvent for dissolving ear waxes and oils.

In addition, most of these "drying" topical solvent liquid base ear drops require the user to remain in awkward sideways positions for dispersing of medication to the ear canal until the liquid solvent dries.

Ointments are base formulations usually homogeneous mixtures, very moisturizing with ~80% oil to 20% water, and are beneficial for dry skin conditions. They have a low risk of sensitization due to formulations having few compounds or ingredients, beyond the base oil or fat, and low irritation risk. There are many general designed classes of mixtures, with no clear dividing line between similar formulations therefore what might be labeled "cream" is in fact an "ointment". They are often disliked by patients due to greasiness.

A cream base formulation typically contains an emulsion of oil and water in almost equal proportions. Creams are user-friendly soft solids or liquids thicker than a lotion and contain medicaments for therapeutic purposes. A cream maintains its shape when removed from its container. Many topical steroid creams are oil-in-water emulsions which penetrate the outer layer of skin. Emulsions are chemical mixtures produced by mechanical blending or mixing of components, may be heterogenous in nature, and may easily be disposed to phase separation of components. Since creams are partially water-based, there is a potential for bacterial growth, contamination, or reduced shelf life of the medicament. Sensitivity to antibiotics and/or the preservatives contained in cream based medicaments is often reported. Adverse reactions to topical hydrocortisone (Cortisol) include burning, itching, irritation, dryness, dermatitis, endocrine side effects, and may affect persons with diabetes or glaucoma since a primary function of hydrocortisone in the body is increasing blood sugar through gluconecogenesis. For example, Cortisporin is available as a cream for ear treatment. It is a combination of two antibiotics Neomycin and Polymyxin B for treating ear canal bacterial infections and the corticosteroid hydrocortisone for reducing inflammation. Reported sensitization reactions to antibiotic neomycin may cause skin sensitization, swelling, or sensitivities of the kidney (nephrotoxicity), cochlea (ear) or auditory nerves (ototoxicity), or may induce excessive glutamate or calcium production (excitotoxicity).

Lotions include liquid base formulations similar to topical solutions but are thicker and more emollient than solvent solutions. Often a lotion contains an oil mixed with water, little to no alcohol, and should be shaken into suspension before use. A colloidal suspension may be a mixture, as an emulsion, where small but undissolved solid particles are suspended and dispersed by molecular motion in the surrounding solvent system.

Lipids are a broad group of naturally occurring molecules which includes fats, waxes, sterols, fat-soluble vitamins, glycerols, and glycerides. Lipids are usually liquid greasy to the touch, soluble in alcohol or ether, insoluble in water, and hydrophobic or amphiphilic molecules. Lipids are basic structural components of living cells and store energy.

Emulsion lotions are a type of suspended solution in which surface tension plays a role between two liquids. Emulsions are also used in making many cosmetic products, or liquid preparations consisting of completely immiscible liquids, one of which forms globules dispersed throughout the other liquid.

Cationic emulsions are used in some pharmaceutical products because of their antimicrobial properties. A colloidal suspension may be a mixture where small but undissolved particles are suspended and dispersed by molecular motion in the surrounding solvent system. Non-ionic emulsions are used in some pharmaceutical products because they have low toxicity. For example, tiny fragments of oil suspended in pure water will spontaneously assemble themselves into much larger masses. Dispersion processes are not well understood and are not purely chemical but are also mechanical. Dispersion is a process by which, in the case of solids, particles become widely or evenly spread throughout a liquid. The smaller the droplet, the greater the surface tension and thus the greater the force to merge with, or perhaps to encapsulate, other lipids. Surfactants decrease surface tension of liquids. Surfactants are usually organic compounds that are amphiphilic, meaning they contain both hydrophobic structural groups and hydrophilic structural groups. Therefore, a surfactant molecule contains both a water insoluble (or oil soluble component) and a water soluble component.

Steroids or sterols are lipids and include any fat-soluble organic compounds derived from plants or animals with specific physiological action. Hydrocortisone is a steroid hormone, or glucocorticoid, produced by the adrenal gland. It is released in response to stress and low blood levels of glucocorticoids to increase blood sugar through gluconeogenesis and counteracts insulin. Hydrocortisone suppresses the immune system, aids in fat, protein and carbohydrate metabolism, and acts as a diuretic hormone. Hydrocortisone is an anti-inflammatory which functions by reducing histamine secretion and stabilizes lysosomal membranes preventing damage to healthy tissue.

BRIEF SUMMARY OF THE INVENTION

The present invention provides a method and formulation for treating ear inflammation caused by "dry ear" or asteatosis. The formulation of the present invention is topically applied to treat asteatosis or "dry ear" in the form of drops of a semi-viscous ear lotion containing the active anti-inflammatory ingredient hydrocortisone.

The formulation of the present invention contains a two-part polyhydroxy solvent base comprising a lipid and glycol used in the present method by applying said formulation mixture as drops, i.e. eardrops, to a person in need of treatment or prevention of "dry ear" symptoms. The polyhydroxy solvent base formulation comprises a lipid and glycol including combinations of glycol, glycerin, sugar alcohols, or lipophilic components. The first component of the base liquid formulation, diglycerin (diglycerol) is a semi-viscous, sticky or glutinous, and hygroscopic lipid which is adsorbed on the skin surface and penetrates the skin. The second component of the formulation of this invention, 1,3-butylene glycol, is a short chain lipophilic alcohol solvent for solubilizing Cortisol and natural products having anti-inflammatory, anti-irritant, and wound healing properties. In the present invention, a new interface or suspension complex is generated between diglycerin and polyhydroxy 1,3-butylene glycol, including the dispersed Cortisol and natural products having anti-inflammatory, anti-irritant, and wound healing properties.

Surfactants are usually amphiphilic organic compounds, meaning they contain both hydrophobic groups and hydrophilic groups. Surfactants reduce surface tension of liquids and improve dispersion of the liquid. In the present invention formulation, a combination of the cationic and nonionic surfactants is used for effective dispersion and delivery of anti-inflammatory hydrocortisone and for higher permeation of lipophilic ingredients thereby decreasing dryness of the sensitive ear canal tissues.

The formulation of this invention may further comprise a compound having a natural anti-irritant, for example an avenanthramide, such as an oat (*Avena Sativa*) kernel extract. The formulation of this invention may further comprise a compound having wound healing activity. For example, Alpha bisabolol, i.e., (+)-epi-bisabolol the wound healing principle of *Peperomia galioides* maybe included in the formulation of the present invention. Alpha bisabolol is also known as a soothing agent. The formulation of this invention may further include an emollient, such as Aloe, which reduces irritation and treats abrasions, minor wounds, and burns. The formulation of this invention also may include a pain reliever such as a White Willow Bark extract which also has anti-inflammatory properties. The formulation of the present invention may comprise a natural humectant such as pyrrolidone carboxylic acid. The present compound may comprise a compound having anti-allergy properties, e.g. a liquorice root extract such as dipotasium glycyrrhizate, which has anti-allergic properties, but also is an anti-inflammatory agent and a surfactant.

The ear drop formulation of the present invention comprises a polyhydroxy solvent, and suspended and dispersed natural products with anti-inflammatory, anti-irritant, and wound healing properties, especially for those persons with hypersensitivities to antibiotics or cream based formulations.

DETAILED DESCRIPTION OF THE INVENTION

The present invention preferably comprises a mixture of natural products having anti-inflammatory, anti-irritant and wound healing properties, (hereinafter "natural ingredients") in a polyhydroxy solvent wherein said solvent is a mixture of one or more glycol compounds, dihydric alcohol compounds, glycerin compounds, trihydric or quadri-hydric alcohol compounds such as diglycerin for treating and preventing the symptoms of "dry ear".

Organic molecules containing a hydroxyl group are known as alcohols and because of their tendency to form hydrogen bonds both as donor and acceptor and the ability to increase hydrophilicity and water solubility; while the tendency of the carbon chain to resist water solubility. For example, alcohols of five or more carbons (are effectively insoluble in water because of the hydrocarbon chain's dominance. However, as in the present invention, polyhydroxy (multiple OH groups) solvents promote both water solubility and hydrocarbon solubility. The diglycerin compound or polyhydroxy quadri-hydric alcohol may comprise glycerin from natural or synthetic sources, preferably from natural sources, lipids, sugar alcohols, or lipophilic compounds. Most preferably, said diglycerin or diglycerol, is 3,3'-oxydipropan-1,2-diol. Diglycerin (diglycerol) is a semi-viscous, sticky, or glutinous hygroscopic liquid emollient which is adsorbed on the skin surface and then penetrates the skin. The glycol compounds may comprise dihydroxyalkyl compounds, such as 1,3 butyleneglycol, ethylene glycol, 1,2 propylene glycol or hydroxyalkyloxyalkyl compounds such hydroxymethyleneoxyethylene glycol, etc. Most preferably, said glycol is 1,3 butyleneglycol, which besides having the necessary solvent properties provides anti-fungal and anti-bacterial properties. In the present invention, nearly equal quantities of Diglycerin 801 and 1,3-butylene glycol form a two part, clear to light yellow color, base formulation. The overall formulation pH between 5.00-5.80 is slightly more acidic than healthy earwax pH of about 6. The overall formulation approximate specific gravity is 1.12+/−0.01, as compared to specific gravity of Diglycerin of 1.332 and 1,3-Butanediol 1.001 (g/cm3).

The natural ingredients of the present invention may comprise from about 0.5 to about 10%, by weight, of said ear drop or lotion formulation. More preferably, said natural ingredients may comprise from about 0.75 to about 5%, by weight, e.g. from about 1 to about 3%, by weight, of said ear drop formulation. The natural ingredients preferably are as follows:

An anti-irritant agent derived from a natural source, e.g. an avenanthramide. A preferred avenanthramide source is a product sold as Drago-Calm available from Syrmise of Teterboro, N.J., 00768. Drago-Cahn is reported to be an Oat (Avena Satvia) Kernel Extract having a guaranteed constituent concentration of 100 ppm avenanthramides. This product has superior anti-irritant and anti-oxidant properties. The Avenanthramides include in this product are analogues of Tranilast™, which is a potent anti-histamine. The anti-irritant agent may comprise from about 0.1 to about 5%, by weight, preferably from 0.5 to about 1.5%, by weight, of the eardrop formulation of this invention.

The formulation of this invention may further comprise one or more compounds having natural wound healing activity for treating and preventing "dry ear". Preferably, said wound healing compounds may comprise Aloe and/or alpha-bisabolol. Aloe is a gel obtained by crushing the mucilaginous cells found in the inner tissue of the plant leaf. Aloe is a wound healing agent and has emollient properties. The emollient effect of this gel is largely attributed to a constituent polysaccharide (glucomannan) similar to guar gum. The term "aloe" refers to a solid residue obtained by evaporating the latex derived from the outer layers of the plant leaf Aloe latex also contains the anthraquinone barbaloin (a glucoside of aloeemodin). Topical application of aloe in the formulation of this invention alleviates irritation, inhibit infection and promote healing of abrasions, minor wounds, and burns. The beneficial effects of aloe gel in relieving skin irritation in dry ear may be due, in part, to its moisturizing activity which reduces drying of abraded or injured skin. Some clinical studies have demonstrated acceleration of wound healing from aloe. Aloe also has anti-inflammatory properties.

Alpha bisabolol or (+) epi-Alpha-bisabolol is a terpenoid which is the wound healing principal of *Peperomia galioides* and also has anti-inflammatory properties. Natural Alpha bisabolol is available from BASF. The wound healing components of the present eardrop formulation, i.e. aloe and/or alpha bisabolol, may comprise from about 0.01 to about 1%, by weight, preferably from about 0.05 to about 0.15%, by weight.

The formulation of the present invention preferably may comprise further anti-inflammatory agents, which agents may, in addition, have anti-allergy and analgesic properties such as salts of glycyrrhic acid, e.g. dipotassium glycyrrhizate and White Willow Bark extract, respectively. The dipotassium glycyrrhizate may be extracted from liquorice root. The bark of the white willow tree is a source of salicin and other salicylic-compounds which are similar in structure to aspirin (acetyl salicylic acid) Native Americans are thought to have used ground willow bark a as a medicinal remedy for everything from pain relief to fevers. Today, white willow bark is often used as a natural alternative aspirin—one of the most common uses in dietary supplements is as a adjunct for weight loss. Thus, the extract of white willow tree bark is utilized in the present formulation as a pain reliever (headaches, arthritis, minor injuries) and an anti-inflammatory agent. The primary active compound in white willow bark is salicin. In the body salicin can be converted into salicylic acid, which has powerful effects as an anti-inflammatory and pain reliever. The anti-inflammatory agents may comprise from about 0.001 to about 1%, by weight of the formulation of this invention, e.g. from about 0.002 to about 0.05%, by weight. The formulation of the present invention may further comprise additional humectants in addition to glycerin discussed above. Preferably, the ear drop formulation of the present invention will comprise a natural humectant such as pyrrolidone carboxylic acid, such as Ajidew N-50 which is the sodium salt of said acid and is available from Ajinomoto USA, Inc. of Paramus, N.J. 07652.

The present invention may include one or more surfactants to stabilize the formulation mixture. Cationic and nonionic surfactants decrease the surface tension of the hygroscopic polyhydroxy solvent. Dispersion of the hydrocortisone, anti-inflammatory, anti-irritant, and wound healing particles in the base formulation compound is enhanced with surfactants. In the present invention, preferably at least one of the surfactants is a cationic surfactant, e.g. a quaternary amine, such as Stepanquat 50 NF which is a dialkyl dimethyl ammonium chloride and is available from Stepan Company. Pathogenic and nonpathogenic bacteria and fungi may dominate the flora of the ear canal causing overgrowth and actual infection and desiccation of ear tissue. Quaternary ammonium compounds act by disrupting cell membranes and are lethal to a wide variety of organisms including fungi, amoeba, and enveloped viruses. Quaternary ammonium salts are also employed as phase transfer catalysts and accelerate reactions between compounds dissolved in immiscible solvents. More preferably, the cationic surfactant stabilized formulation additionally includes a nonionic surfactant such as Tween 20 which is known to lower surface viscosity without significantly changing material absorbed in solution. Tween 20, polysorbate 20, is a relatively non-toxic emulsifier and promotes suspension and dispersion of particles and solids in the glycerol base formulation. In the present invention, the surfactants may comprise from about 0.25% Tween 20 and from about 0.10% Stepanquat 50 NF by weight of said formulation mixture, more preferably from about 0.2 to about 0.45% by weight.

Steroids or sterols are lipids and include any fat-soluble organic compounds derived from plants or animals with specific physiological action. Hydrocortisone is a steroid hormone, or glucocorticoid, produced by the adrenal gland. It is released in response to stress and low blood levels of glucocorticoids to increase blood sugar through gluconeogenesis and counteracts insulin. Hydrocortisone suppresses the immune system, aids in fat, protein and carbohydrate metabolism, and acts as a diuretic hormone. Hydrocortisone is an anti-inflammatory by reducing histamine secretion and stabilizes lysosomal membranes preventing damage to healthy tissue. Hydrocortisone is available without prescription with the base formulations as creams and ointments. In the present invention, hydrocortisone may comprise from about 0.2375% to about 0.2625% by weight of said formulation, more preferably from about 0.2250% to about 0.2750% by weight.

The formulation below discloses a preferred embodiment of this invention and the sources of the individual components Part A preparation of base formulation includes a 1,3-Butylene Glycol, Diglycerin 801, Drago-Calm, Ajidew N-50.

Preparation of the colloidal suspension in base solvent 1,3-butylene glycol includes all Part B Ingredients heated to 45° C. until all the solids are dissolved and the batch is uniform. Part B is then added to Part A and mixed until uniform and as the specifications indicate, may include approximately 53.00+/−1.00% solids. A colloidal suspension includes one liquid in another liquid wherein minute globules may be dispersed throughout one of the liquids. The tables below disclose a preferred embodiment of this invention and the sources of the individual components.

PERCENTAGE FORMULA

| Component | Source | % By Weight |
|---|---|---|
| 1,3-Butylene Glycol | Ashland | 47.5800 |
| Diglycerin 801 | U.S. Cosmetics | 50.0000 |
| Drago-Calm | Symrise | 1.0000 |
| Ajidew N-50 | Ajinomoto | 0.5000 |
| ABS White Willow Bark Extract, powder | Active Concepts | 0.0100 |
| OriStar DPG | Orient Stars | 0.2000 |
| Stepanquat 50 NF | Stepan | 0.1000 |
| alpha-Bisabolol, natural | BASF | 0.1000 |
| Tween 20 | Uniqema | 0.2500 |
| Hydrocortisone | Alfa Chem | 0.2500 |
| ActiveAloe, #AA1210A | Aloe Corp. | 0.0100 |
| | | 100.0000% |

COMPOUNDING FORMULA
Batch Size: 1,000 lbs.

| | By Weight in lbs. |
|---|---|
| PART A | |
| 1,3-Butylene Glycol | 425.8000 |
| Diglycerin 801 | 500.0000 |
| Drago-Calm | 10.0000 |
| Ajidew N-50 | 5.0000 |
| PART B | |
| 1,3-Butylene Glycol | 50.0000 |
| ABS White Willow Bark Extract, powder | 0.1000 |
| OriStar DPG | 2.0000 |
| Stepanquat 50 NF | 1.0000 |
| alpha-Bisabolol, natural | 1.0000 |
| Tween 20 | 2.5000 |
| Hydrocortisone | 2.5000 |
| ActivAloe, #AA1210A | 0.1000 |
| | 1,000.0000 lbs. |

COMPOUNDING PROCEDURE

| | |
|---|---|
| Part A | Add Butylene Glycol into the main processing tank. Add the remaining Part A ingredients. Mix until uniform. |
| Part B | In a separate tank, heat Part B Ingredients to 45° C. Mix until all the solids are dissolved and the batch is uniform, Add Part B to Part A. Mix until uniform. Sample for QC check. |

SPECIFICATIONS

| | |
|---|---|
| Color: | Colorless to light straw (to match standard) |
| Odor: | Characteristic (to match standard) |
| Appearance: | Clear, semi-viscous liquid |
| pH at 25° C. (10% Solution): | 5.00-5.80 |
| Specific Gravity at 25/25° C.: | 1.12 +/− 0.01 |
| Viscosity (cps) at 25° C.; (RVT: #4 spindle a@ 10 rpm) | 700-1,000 |
| Total Aerobic Plate Count: (Including Yeast & Mold) | Less than 100 cfu per gram |
| Gram Negative Bacteria: | Absent |

| Assay: Hydrocortisone | RELEASE | ACTUAL |
|---|---|---|
| | 0.2375%-0.2625% | 0.2250%-0.2750% |

Supplementary Tests:

| | |
|---|---|
| IR | to match standard |
| % Solids: | 53.00 +/− 1.00 |

| INGREDIENTS LISTING |
| --- |
| ACTIVE INGREDIENTS: |
| Hydrocortisone (0.25%) |
| INACTIVE INGREDIENTS: |
| Diglycerin |
| Butylene Glycol |
| *Avena Sativa* (Oat) Kernel Extract |
| Sodium PCA |
| alpha-Bisabolol |
| Dipotassium Glycyrrhizate |
| *Aloe Barbadensis* Leaf Juice |
| *Salix Alba* (Willow) Bark Extract |
| Benzalkonium Chloride |
| Glycerin |
| Water (Aqua) |
| Polysorbate 20 |

What is claimed is:

1. A method of treating chronic otitis externa in a human that is suffering therefrom, comprising topically applying to the ear canal of said human a polyhydroxy based formulation comprising:
   (a) an anti-irritant agent wherein said anti-irritant agent is avenanthramide;
   (b) a wound healing agent wherein said wound healing agent is aloe;
   (c) an anti-inflammatory agent wherein said anti-inflammatory agent is dipotassium glycyrrhizate;
   (d) a pain reliever wherein said pain reliever is a white willow bark extract;
   (e) a humectant wherein said humectant agent is a pyrrolidone carboxylic acid;
   (f) a polyhydroxy liquid solvent stabilized with a cationic surfactant and a nonionic surfactant; and
   (g) an active ingredient wherein said active ingredient is hydrocortisone;
   wherein the polyhydroxy based formulation comprises a pH range from about 5.0 to about 5.8 and a specific gravity that is 1.12+/−0.01.

2. The method of claim 1 wherein said polyhydroxy liquid solvent comprises 1,3-butylene glycol and diglycerin.

3. The method of claim 1 wherein said cationic surfactant is the quaternary amine dialkyl dimethyl ammonium chloride.

4. The method of claim 1 wherein said liquid formulation comprises from about 0.1 to about 5% of an anti-irritant agent, 0.01 to about 1% of a wound healing agent, 0.001 to about 1% of an anti-inflammatory agent, and 0.22% to about 0.28% hydrocortisone.

5. The method of claim 1 wherein said polyhydroxy based formulation further comprises a mixture containing about 3.1% solids.

6. The method of claim 1 wherein said formulation is applied in the form of ear drops to the ear canal of the human.

7. The method of claim 1 wherein said polyhydroxy liquid solvent further comprises a lipid and glycol lubricating hydrophilic base formulation including combinations of glycol, glycerin, sugar alcohols, or lipophilic compounds for reducing surface tension and for improving tissue surface adsorption.

8. A method of treating and reducing the risk of chronic otitis externa in a mammal in need thereof by topically applying to the ear canal of said mammal a formulation comprising:
   (a) an anti-irritant agent wherein said anti-irritant agent is avenanthramide;
   (b) a wound healing agent wherein said wound healing agent is aloe;
   (c) an anti-inflammatory agent wherein said anti-inflammatory agent is dipotassium glycyrrhizate;
   (d) a pain reliever wherein said pain reliever is a white willow bark extract;
   (e) a humectant wherein said humectant agent is a pyrrolidone carboxylic acid;
   (f) a polyhydroxy liquid solvent stabilized with a cationic surfactant and a nonionic surfactant; and
   (g) an active ingredient wherein said active ingredient is hydrocortisone;
   wherein the formulation comprises a pH range from about 5.0 to about 5.8 and a specific gravity that is 1.12+/−0.01.

9. The method of claim 8 wherein said polyhydroxy liquid solvent comprises 1,3-butylene glycol and diglycerin.

10. The method of claim 8 wherein said cationic surfactant is the quaternary amine dialkyl dimethyl ammonium chloride.

11. The method of claim 8 wherein said liquid formulation comprises from about 0.1 to about 5% of an anti-irritant agent, 0.01 to about 1% of a wound healing agent, 0.001 to about 1% of an anti-inflammatory agent, and 0.22% to about 0.28% hydrocortisone.

12. The method of claim 8 wherein said polyhydroxy based formulation further comprises a mixture containing about 3.1% solids.

13. The method of claim 8 wherein said formulation is applied in the form of ear drops to the ear canal of the human.

14. The method of claim 8 wherein said polyhydroxy liquid solvent further comprises a lipid and glycol lubricating hydrophilic base formulation including combinations of glycol, glycerin, sugar alcohols, or lipophilic compounds for reducing surface tension and for improving tissue surface adsorption.

* * * * *